United States Patent [19]

Ishikawa

[11] Patent Number: 5,601,620
[45] Date of Patent: Feb. 11, 1997

[54] ACIDIC HAIR DYE COMPOSITIONS WHICH COMPRISE ACID DYES, BENZYL ALCHOL, AND POLYSILOXANES

[75] Inventor: Hiroshi Ishikawa, Yokohama, Japan

[73] Assignee: Shiseido Company Ltd., Tokyo, Japan

[21] Appl. No.: 442,941

[22] Filed: May 17, 1995

Related U.S. Application Data

[63] Continuation of Ser. No. 937,895, filed as PCT/JP92/00147, Feb. 14, 1992, published as WO92/14441, Nov. 9, 1992, abandoned.

[30] Foreign Application Priority Data

Aug. 20, 1991 [JP] Japan .................................. 3-232189
Feb. 14, 1992 [JP] Japan .................................. 3-42354

[51] Int. Cl.⁶ ........................................ A61K 7/13
[52] U.S. Cl. .................... 8/405; 8/435; 8/552; 8/581; 8/611
[58] Field of Search ............................ 8/405, 421, 423, 8/435, 552, 581, 611

[56] References Cited

U.S. PATENT DOCUMENTS

| | | | |
|---|---|---|---|
| 3,630,654 | 12/1971 | Rosenthal et al. | 8/405 |
| 3,912,808 | 10/1975 | Sokol | 8/405 |
| 3,986,825 | 10/1976 | Sokol | 8/406 |
| 4,567,039 | 1/1986 | Stadnick et al. | 8/405 |
| 4,749,565 | 6/1988 | Grollier | 8/405 |
| 4,842,849 | 6/1989 | Grollier et al. | 8/405 |
| 4,873,079 | 10/1989 | Hahn et al. | 8/405 |
| 4,957,731 | 9/1990 | Helioff et al. | 8/405 |
| 5,015,263 | 5/1991 | Albrecht et al. | 8/409 |
| 5,104,413 | 4/1992 | Ikeda | 8/405 |
| 5,254,333 | 10/1993 | Kojino et al. | 8/405 |

FOREIGN PATENT DOCUMENTS

| | | |
|---|---|---|
| 0132960 | 2/1985 | European Pat. Off. . |
| 0429855 | 6/1991 | European Pat. Off. . |
| 0470381 | 2/1992 | European Pat. Off. . |
| 3413125 | 10/1984 | Germany . |
| 2173515 | 10/1986 | United Kingdom . |

OTHER PUBLICATIONS

Japanese Abstract, 57–192310, Nov. 1982.
Japanese Abstract, 59–190910, Oct. 1984.
S.T.N. File Supplier, Karlsruhe, DE, File Chemical Abstracts, vol. 117, CA117(18):178088g, JP04074113 A2 (Abstract), Mar. 9, 1992.

*Primary Examiner*—Paul Lieberman
*Assistant Examiner*—Caroline L. Dusheck
*Attorney, Agent, or Firm*—Sprung Horn Kramer & Woods

[57] ABSTRACT

An acid dye composition for hair containing (i) 0.01–5.0% by weight of at least one silicone, or (ii) 0.001–0.1% by weight of dye and 1% by weight or more of benzyl alcohol based upon the total amount of the composition.

5 Claims, No Drawings

ACIDIC HAIR DYE COMPOSITIONS WHICH COMPRISE ACID DYES, BENZYL ALCHOL, AND POLYSILOXANES

This application is a continuation of application Ser. No. 07/937,895, filed as PCT/JP92/00147, Feb. 14, 1992, published as WO92/14441, Mar. 9, 1992, now abandoned.

TECHNICAL FIELD

The present invention relates to an acid dye composition for hair, and more specifically it relates to an acid dye composition for hair capable of finishing the hair having a favorable texture after use, while satisfying the essential requirements of an acid hair dye, including anti-washing properties. The present invention also relates to an acid dye composition for hair having improved dyeing properties in a system containing a small amount of dye to be formulated.

BACKGROUND ART

Hair dye compositions of the prior art include oxidizing type hair dyes that perform dyeing using an oxidation-reduction reaction, and acid hair dyes that perform dyeing in the acidic region using a dye prescribed by law. Among these, the main ingredients of acid hair dyes consist of acid dyes, alcohols (typically benzyl alcohol), organic solvents and a pH-controlling acids (typically citric acid). These are formulated with a thickener so as to prevent the dye from running off the hair during use. Since these hair dye compositions normally involve single preparations, they have the advantage of being easier to use compared with oxidizing hair dyes that require two or more preparations. However, the optimum pH range of acid hair dyes is 1.5–4.5 (Note: this range is preferable for obtaining favorable dyeing properties and washability, with an average pH range of around 3 being preferable). Since this pH is considerably low with respect to ordinary cosmetic products for the hair, this type of hair dye composition has a disadvantage in that it often imparts an unsatisfactory feeling during application thereof.

On the other hand, as acid hair dyes are single preparations, a possible application that takes advantage of that characteristic is a combined rinse and hair dye composition usable after shampooing. In addition, in the case of such a composition, both rinsing and dyeing can be performed simultaneously, making it extremely useful as an easy-to-use, convenient hair dye preparation. In order to realize a combined rinse and hair dye composition, it is necessary that the composition contain a small but sufficient amount of dyes so that the dyes do not remain on the hands after shampooing. However, when the amount of dyes is simply reduced, the dyeing properties become inadequate whereby the composition is prevented from demonstrating its initial effects.

DISCLOSURE OF INVENTION

The objects of the present invention are to provide an acid dye composition for hair, in consideration of the above-mentioned circumstances of the prior art, that is, capable of producing a favorable texture after use, while satisfying the essential requirements of an acid hair dye, including, for example, anti-washability.

In addition, another object of the present invention is to provide an acid dye composition for hair that possesses satisfactory dyeing properties, in terms of practical use, when the amount of dye formulated into the composition is reduced.

In accordance with the present invention, there is provided an acid dye composition for hair wherein at least one silicone is formulated into an amount of 0.01–5.0% by weight based on the total amount of the composition.

In accordance with the present invention, there is also provided an acid dye composition for hair, wherein 0.001–0.1% by weight of dye and 1% by weight or more of benzyl alcohol are blended into the composition.

BEST MODE FOR CARRYING OUT THE INVENTION

The composition of the present invention preferably further comprises 5% by weight or more of at least one compound selected from the group consisting of polyols, levulinic acid, N-methylpyrrolidone or tetrahydrofurfuryl alcohol. Among these, polyols are particularly preferable.

According to the present invention, by formulating 0.01–5% by weight, and preferably 1.0–3.0% by weight, of a silicone into an acid hair dye composition, the feeling during use is remarkably improved and the dyeing properties of the coloring dyes are enhanced. In addition, the composition of the present invention can also be applied as a combined rinse and hair dye composition used after shampooing by taking advantage of its single-preparation characteristic.

Examples of the silicones used in the present invention are indicated as follows. One or more of these silicones may be used, in combination, in the composition of the present invention.

(A) Dimethylpolysiloxane

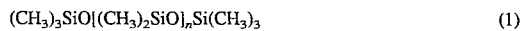

$$(CH_3)_3SiO[(CH_3)_2SiO]_nSi(CH_3)_3 \quad (1)$$

wherein, in the formula (1), n is an integer of 3–650.

(B) Methylphenylpolysiloxane

$$(CH_3)_3SiO(\underset{\underset{CH_3}{|}}{\overset{\overset{C_6H_5}{|}}{Si}}O)_nSi(CH_3)_3 \quad (2)$$

$$(CH_3)_3SiO[(CH_3)_2SiO]_n[(C_6H_5)_2SiO]_mSi(CH_3)_3 \quad (3)$$

wherein, in the formula (2), n is an integer from 1–500, and in the formula (3), the sum of m and n is an integer of 1–500.

(C) Polyether denatured polysiloxane

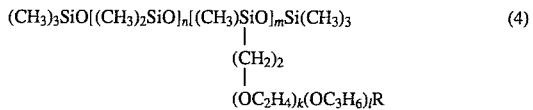

$$(CH_3)_3SiO[(CH_3)_2SiO]_n[(CH_3)SiO]_mSi(CH_3)_3 \quad (4)$$
$$\qquad\qquad\qquad\qquad\qquad\quad |$$
$$\qquad\qquad\qquad\qquad\qquad (CH_2)_2$$
$$\qquad\qquad\qquad\qquad\qquad\quad |$$
$$\qquad\qquad\qquad\qquad\quad (OC_2H_4)_k(OC_3H_6)_lR$$

wherein, in the formula (4). R represents an alkyl group having 1–12 carbon atoms, an alkoxy group having 1–6 carbon atoms or a hydroxyl group, n represents an integer of 1–100 and preferably 20–30, m represents an integer of 1–20 and preferably 2–10, k represents an integer of 0–50 and preferably 20–30, and l represents an integer of 0–50 and preferably 20–30.

(D) Amino modified polysiloxane

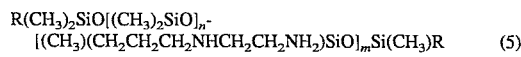

$$R(CH_3)_2SiO[(CH_3)_2SiO]_{n^-}$$
$$[(CH_3)(CH_2CH_2CH_2NHCH_2CH_2NH_2)SiO]_mSi(CH_3)R \quad (5)$$

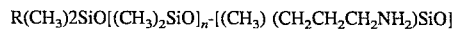

$$R(CH_3)_2SiO[(CH_3)_2SiO]_{n^-}[(CH_3)(CH_2CH_2CH_2NH_2)SiO]$$

(6)

wherein, in the formulae (5) and (6), R represents a methyl group or methoxy group, n represents an integer of 1–500, and m represents an integer of 1–50.

(E) Epoxy modified polysiloxane

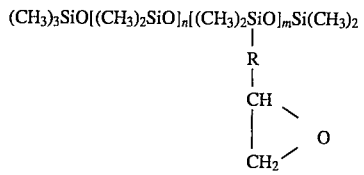(7)

wherein in the formula (7), R represents an alkylene group having 1–3 carbon atoms, n represents an integer of 1–500 and m represents an integer of 1–50.

(F) Fluorine modified polysiloxane

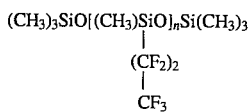(8)

wherein, in the formula (8), n represents an integer of 1–400 and m represents an integer of 1–250.

(G) Alcohol modified polysiloxane

(9)

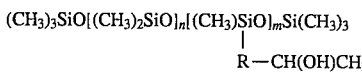(10)

wherein, in the formulae (9) and (10), R is absent or represents an alkylene group having 1–4 carbon atoms, and n and m represent integers of 1–500 and 1–200, respectively.

(H) Alkyl modified polysiloxane

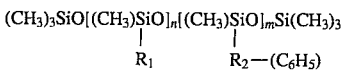(11)

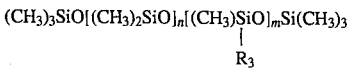(12)

wherein, in the formulae (11) and (12), $R_1$ represents an alkyl group having 2–18 carbon atoms, $R_2$ is absent or represents an alkylene group having 1–4 carbons, $R_3$ represents an alkyl group having 10–16 carbons, and n and m are integers of 1–500 and 1–200, respectively.

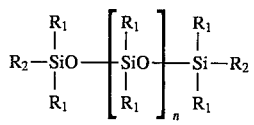(13)

wherein, in the formula (13), $R_1$ represents a methyl group or partially represents a phenyl group, $R_2$ represents a methyl group or hydroxyl group, and n represents an integer of 3,000–20,000.

When at least one silicone selected from the group consisting of the above-mentioned silicones, especially methylphenylpolysiloxane (for example, Silicone KF56: Shin-Etsu Chemical Co., Ltd.) and dimethylsiloxane-methyl(polyoxyethylene)siloxane copolymer(having an E.O. (i.e., mean number of moles added, same as hereinafter)= 20–30) (for example, Silicone SC-9450: Shin-Etsu Chemical Co., Ltd.), is used, a composition is obtained that not only enhances the feeling thereof during application but also has improved dyeing properties and is superior in the stability thereof, In addition, a specific example of high polymer silicone is a rubber-like dimethylpolysiloxane (degree of polymerization n=5000–8000: Shin-Etsu Chemical Co., Ltd.).

The formulating amount of the above-mentioned silicones is 0.01–5.0% by weight of the total amount of the composition. When the formulating amount of the silicones is less than 0.01% by weight, the desired effects cannot be obtained, while when the formulating amount of silicones is more than 5.0% by weight, the composition becomes sticky resulting in an unpleasant feeling upon application thereof.

Moreover, according to the present invention, an acid hair dye composition comprises 0.001–0.1% by weight, and preferably 0.01–0.05% by weight, of dye, and 1% by weight or more, and preferably 2.0–5.0% by weight, of benzyl alcohol.

Although the formulating amount of dye in the conventional hair dye compositions is 0.5–1% by weight, the formulating amount of dye can be 0.001–0.1% by weight in the present invention. The reduction in dyeing properties owing to the reduced amount of hair dye is compensated for by the addition of 1% by weight or more of benzyl alcohol according to the present invention. Moreover, the present composition is in the form of a rinse type of hair dye also having favorable dyeing properties. When the formulating amount of benzyl alcohol is less than 1% by weight, satisfactory dyeing properties cannot be obtained. Although there is no particular upper limit on the formulating amount of benzyl alcohol, a formulating amount of up to 10% by weight is usually appropriate. This is because even if the formulating amount of benzyl alcohol exceeds 10% by weight, effects corresponding to formulating amounts beyond that level are not obtained. On the contrary, large formulating amounts of benzyl alcohol result in the separation of the system leading to a possible loss of stability, which is undesirable.

Also, according to the present invention, it is preferable to formulate 1% by weight or more of benzyl alcohol as well as 5% by weight or more of at least one compound selected from polyols, levulinic acid, N-methylpyrrolidone or tetrahydrofurfuryl alcohol since these compounds further improve the stability of the system as well as the dyeing effects. These effects are particularly remarkable when the formulating amount of benzyl alcohol is 3% by weight or more. Among these compounds, polyols are particularly preferable. Examples of such polyols include ethyl cellosolve, methyl ethyl carbitol, 1,3-butylene glycol, dipropylene glycol and propylene glycol. Although there is no particular upper limit on the formulating amounts of polyols, levulinic acid, N-methylpyrrolidone and/or tetrahydrofurfuryl alcohol, a total formulating amount of up to 30% by weight is suitable. If the total blended amount of these compounds exceeds 30% by weight, the dyeing properties tend to worsen resulting in the dye coming off easily.

Moreover, one or more cationic compounds can be optionally formulated into the first hair dye composition of the present invention. Examples of said cationic compounds include poly(dimethyldiallyl ammonium halide) type cationic polymers, cationic polymers that are condensation products of taloyl amines obtained from polyethylene glycol, epichlorohydrin, propylene amine and tallow fatty acid, and/or condensation products of cocoyl amines obtained from polyethylene glycol, epichlorohydrin, propylene amine and oils and fats, vinylpyrrolidone-dimethylaminoethyl methacrylate copolymer cationic polymers and quaternary nitrogen-containing cellulose ether type cationic polymers containing quaternary nitrogen.

By formulating such cationic compounds, hair becomes more supple and the texture after use is further improved than the case when silicone is used alone.

Moreover, acid dyes, alcohols, organic solvents, acids for controlling pH and thickeners, etc., can be optionally formulated in the first acid hair dye composition of the present invention. The following provides an explanation of these constituent substances.

Coloring materials prescribed by law listed in "Ministerial Ordinance Stipulating Tar Colors able to be Used in Pharmaceuticals, Etc.", that are allowed to be used for the coloring of prescription medicines, quasi drugs and cosmetic compositions while not demonstrating effects harmful to the body, are extremely effective for the dye used in the present invention. A formulating amount of said dye of 0.01–2.0% by weight is preferable. In addition, in the case of using the present invention as a combined rinse and hair dye composition, 0.001–0.1% by weight is suitable for the formulating amount of dye.

Specific examples of dyes capable of being used in the present invention include Red Dye No. 3 (erythrosine), Red Dye No. 102 (newcocin), Red Dye No. 106 (acid red), Red Dye No. 201 (lithol rubine B), Red Dye No. 227 (fast acid magenta), Red Dye No. 230 (1) (erythrosine YS), Red Dye No. 230(2) (erythrosine YSK), Red Dye No. 231 (phloxine BK), Red Dye No. 232 (rose bengal K), Red Dye No. 401 (violamine R), Red Dye No. 502 (ponceau 3R), Red Dye No. 503 (ponceau R), Red Dye No. 504 (ponceau SX), Red Dye No. 506 (fast red S), Orange Dye No. 202 (uranine K), Yellow Dye No. 402 (polar yellow 56), Yellow Dye No. 403(1) (naphthol yellow S), Yellow Dye No. 406 (methanil yellow), Green Dye No. 3 (fast green FCF), Green Dye No. 201 (alizarine cyanine green F), Green Dye No. 204 (pyranine conc), Green Dye No. 205 (light green SF yellow), Yellow Dye No. 401 (naphthol green B), Green Dye No. 402 (guinea green B), Blue Dye No. 1 (brilliant blue FCF), Blue Dye No. 2 (indigo carmine), Blue Dye No. 202 (patent blue NA), Blue Dye No. 205 (alfazurine FG), and Brown Dye No. 201 (resorcine brown).

Examples of alcohols usable in the present invention include aliphatic alcohols, aromatic alcohols and polyatomic alcohols (that are poorly soluble in water) consisting of n-butyl alcohol, sec-butyl alcohol, cyclohexanol, butyl cellosolue benzyl alcohol, 2-phenoxyethanol and phenyl ethanol. 3–10% by weight of at least one alcohol selected from these groups can be formulated into the composition of the present invention.

Examples of organic solvents usable in the present invention include cyclic ketones and ethers such as tetrahydrofurfuryl alcohol, n-methylpyrrolidone and ethylene carbonate, and polyols such as methylethyl: carbitol, 1,3-butylene glycol, dipropylene glycol and propylene glycol. 10–50% by weight of at least one organic solvent selected from these groups can be formulated into the composition of the present invention.

Acids for controlling the pH usable in the present invention include organic acids such as citric acid, malic acid, acetic acid, lactic acid, oxalic acid, tartaric acid, formic acid and levulinic acid, and inorganic acids such as phosphoric acid and hydrochloric acid. The amount formulated is normally such that the pH of the composition is within a range of 1.5–4.5.

Although examples of a thickener usable in the present invention include methyl cellulose, ethyl cellulose, hydroxyethyl cellulose and xanthan gum, the thickener usable in the present invention is not limited to these.

Moreover, in addition to the above-mentioned formulating ingredients, the use of the nonionic surfactants of polyoxyethylene (E.O.=10–30 moles) 2-octyldodecyl ether and polyoxyethylene hydrogenated castor oil ether (E.O.= 40–60 moles) is effective for dispersing and solubilizing agents for the silicones.

In addition to the above-mentioned ingredients, the hair dye of the present invention can be formulated with antiseptics, chelating agents and fragrances as long as the amounts formulated are within a range that does not impair the stability or pH of the composition.

The above-mentioned other ingredients can be optionally used in the same manner as the above-mentioned first composition of the present invention in the second acid hair dye composition of the present invention. An example of said ingredients includes one or more types of cationic compounds. Examples of said cationic compounds include poly(dimethyldiallyl ammonium halide) type cationic polymers, cationic polymers that are condensation products of taloyl amines obtained from polyethylene glycol, epichlorohydrin, propylene amine and tallow fatty acid, and/or condensation products of cocoyl amines obtained from polyethylene glycol, epichlorohydrin, propylene amine and oils and fats, vinylpyrolidone-dimethylaminoethyl methacrylate copolymer cationic polymers and quaternary nitrogen-containing cellulose ether cationic polymers. By formulating the cationic compounds as those indicated above, hair becomes more supple and the texture after use is further improved than when silicone is used alone.

Moreover, acid dye, alcohols, organic solvent, acid for the controlling pH and thickener, etc., can be optionally formulated in the second acid hair dye composition of the present invention. The following provides an explanation of these constituent substances.

Coloring matters prescribed by law listed in "Ministerial Ordinance Stipulating Tar Colors able to be Used in Pharmaceuticals, Etc.", that are allowed to be used for the coloring of prescription medicines, quasi drugs and cosmetic compositions while not demonstrating effects harmful to the body, are extremely effective for the dye used in the present invention. A formulating amount of said dye of 0.01–2.0% by weight is preferable. In addition, in the case of using the present invention as a combined rinse and hair dye composition, 0.001–0.1% by weight is suitable for the formulating amount of dye.

Specific examples of dyes capable of being used in the present invention include Red Dye No. 3 (erythrosine), Red Dye No. 102 (newcocin), Red Dye No. 106 (acid red), Red Dye No. 201 (lithol rubine B), Red Dye No. 227 (fast acid magenta), Red Dye No. 230(1) (erythrosine YS), Red Dye No. 230(2) (erythrosine YSK),Red Dye No. 231 (phloxine BK), Red Dye No. 232 (rose bengal K), Red Dye No. 401(violamine R), Red Dye No. 502 (ponceau 3R), Red Dye No. 503 (ponceau R), Red Dye No. 504 (ponceau SX), Red Dye No. 506 (fast red S), Orange Dye No. 202 (uranine K), Yellow Dye No. 402 (polar yellow 56), Yellow Dye No. 403(1) (naphthol yellow S), Yellow Dye No. 406 (methanil yellow), Green Dye No. 3 (fast green FCF), Green Dye No. 201 (alizarine cyanine green F), Green Dye No. 204 (pyranine conk), Green Dye No. 205 (light green SF yellow), Yellow Dye No. 401 (naphthol green B), Green Dye No. 402 (guinea green B), Blue Dye No. 1 (brilliant blue FCF), Blue Dye No. 2 (indigo carmine), Blue Dye No. 202 (patent blue NA), Blue Dye No. 205 (alphazurine FG), and Brown Dye No. 201 (resorcine brown).

Examples of alcohols usable in the present invention include aliphatic alcohols, aromatic alcohols and polyatomic alcohols (that are poorly soluble in water) consisting of n-butyl alcohol, sec-butyl alcohol, cyclohexanol, butyl Cello solue, benzyl alcohol, 2-phenoxyethanol and phenyl ethanol. 3–10% by weight of at least one alcohol selected from these groups can be formulated into the composition of the present invention.

Examples of organic solvents usable in the present invention include cyclic ketones and ethers such as ethylene carbonate. 10–50% by weight of at least one organic solvent selected from these groups can be formulated into the hair dye composition of the present invention.

Acids for controlling the pH usable in the present invention include organic acids such as citric acid, malic acid, acetic acid, lactic acid, oxalic acid, tartaric acid, formic acid and levulinic acid, and inorganic acids such as phosphoric acid and hydrochloric acid. The amount formulated is normally such that the pH of the composition is within a range of 1.5–4.5.

Although examples of a thickener usable in the present invention include methyl cellulose, ethyl cellulose, hydroxyethyl cellulose and xanthan gum, the thickener usable in the present invention is not limited to these.

In addition to the above-mentioned ingredients, the hair dye of the present invention can be formulated with antiseptics, chelating agents and fragrances as long as the amounts formulated are within a range which does not impair the stability or the pH of the composition.

EXAMPLES

The present invention will now be further illustrated by, but is by no means limited to, the following Examples and Comparative Examples.

Experiment 1

| Formulation | |
| --- | --- |
| Black Dye No. 401 | 0.2(%) |
| Purple Dye No. 401 | 0.3 |
| Yellow Dye No. 4 | 0.1 |
| Benzyl alcohol | 5.0 |
| Tetrahydrofurfuryl alcohol | 12.0 |
| Citric acid | 2.0 |
| Methylphenylpolysiloxane | 1.0 |
| Polyoxyethylene hydrogenated castor oil 40 E.O. | 1.0 |
| Hydroxyethyl cellulose | 3.0 |
| Purified water | Balance |

Preparation Method

A mixture of tetrahydrofurfuryl alcohol, benzyl alcohol, methylphenyl polysiloxane and polyoxyethylene hydrogenated castor oil 40 E.O. (Nippon Emulsion Co., Ltd., Emalex HCl-40) was dissolved in purified water, followed by the gradual addition of hydroxyethyl cellulose to prepare a viscous liquid. Black Dye No. 401, Purple Dye No. 401 and Yellow Dye No. 4 were then added to this viscous liquid after which the pH was adjusted to 2.8–3.0 with citric acid to obtain a uniform viscous liquid.

Comparative Example 1

| Formulation | |
| --- | --- |
| Black Dye No. 401 | 0.2(%) |
| Purple Dye No. 401 | 0.3 |
| Yellow Dye No. 4 | 0.1 |
| Benzyl alcohol | 5.0 |
| Tetrahydrofuryl alcohol | 12.0 |
| Citric acid | 2.0 |
| Hydroxyethyl cellulose | 3.0 |
| Polyoxyethylene hydrogenated castor oil 40 E.O. | 1.0 |
| Purified water | Balance |

Preparation Method

A hair dye was manufactured in the same manner as the above-mentioned Example 1, except that methylphenyl polysiloxane was not formulated.

Effect

The hair dyes obtained in Example 1 and Comparative Example 1 were actually used by six panel having hair streaked with gray. The evaluation results obtained are shown in Table 1.

TABLE 1

| Evaluation Item | Evaluation Results | | | |
| --- | --- | --- | --- | --- |
| | Example 1 | | Comparative Example 1 | |
| Texture | Very supply | 5 | Very supple | 0 |
| | Somewhat supple | 1 | Somewhat supple | 1 |
| | Not supple | 0 | Not supple | 5 |

In addition, with respect to dyeing properties, although both compositions dyed the hair to a dark brown color, the coloring in the case of those panels who used the composition of the Example was more uniform and had a deeper finish, thus making it superior in terms of dyeing properties. In addition, the composition of the Example was also superior with respect to washability.

Examples 2–7

Hair dyes were prepared in the same manner as Example 1 using the types of silicone listed in Table 2. Stability was evaluated after allowing the dyes to stand for 1 month in a constant temperature bath at 50° C. The formulated amounts are shown in Table 2, and the evaluation results are shown in Table 3.

TABLE 2

| | Formulated Amounts of Examples 2–7 | | | | | |
| --- | --- | --- | --- | --- | --- | --- |
| Example No. | 2 | 3 | 4 | 5 | 6 | 7 |
| Black Dye No. 401 | 0.2 | 0.2 | 0.2 | 0.2 | 0.2 | 0.2 |
| Purple Dye No. 401 | 0.3 | 0.3 | 0.3 | 0.3 | 0.3 | 0.3 |
| Yellow Dye No. 4 | 0.1 | 0.1 | 0.1 | 0.1 | 0.1 | 0.1 |
| Benzyl alcohol | 5.0 | 5.0 | 5.0 | 5.0 | 5.0 | 5.0 |
| Tetrahydrofurfuryl alcohol | 12.0 | 12.0 | 12.0 | 12.0 | 12.0 | 12.0 |

TABLE 2-continued

| | Formulated Amounts of Examples 2–7 | | | | | |
|---|---|---|---|---|---|---|
| Example No. | 2 | 3 | 4 | 5 | 6 | 7 |
| Citric acid | 2.0 | 2.0 | 2.0 | 2.0 | 2.0 | 2.0 |
| Methyl polysiloxane | — | — | 1.0 | — | — | — |
| Methylphenyl polysiloxane | 1.0 | 0.5 | — | — | — | — |
| Methylhydrogen polysiloxane | — | — | — | 1.0 | — | — |
| Dimethylsiloxane-methyl (polyoxyethylene) siloxane copolymer (E.O. = 12) | — | — | — | — | 1.0 | — |
| Dimenthylsiloxane-methyl (polyoxycthylene) siloxane copolymer (E.O. = 24) | — | 0.5 | — | — | — | — |
| Dimethylsiloxane-methyl (polyoxyethylene) siloxane copolymer (E.O. = 40) | — | — | — | — | — | 1.0 |
| Polyoxyethylene hydrogenated caster oil 40 E.O. | — | 1.0 | — | — | — | — |
| Polyoxyethylene (E.O. = 16) 2-octyldodecyl ether | 1.0 | — | 1.0 | 1.0 | 1.0 | 1.0 |
| Hydroxyethyl cellulose | 2.0 | 2.0 | 2.0 | 2.0 | 2.0 | 2.0 |
| Purified water | Balance | Balance | Balance | Balance | Balance | Balance |

TABLE 3

| | Evaluation of Examples 2–7 | | | | | |
|---|---|---|---|---|---|---|
| Example No. | 2 | 3 | 4 | 5 | 6 | 7 |
| Stability | ++ | ++ | + | + | + | ++ |
| Dyeing Properties | Good | Good | Good | Good | Good | Good |
| Usability | ++ | ++ | ++ | ++ | ++ | + |

Stability:
++ No separation at all
+ Some separation
Usability:
++ Very smooth
+ Somewhat smooth

Example 8

Color Rinse Type Hair Dye

| Formulation | |
|---|---|
| Black Dye No. 401 | 0.03(%) |
| Purple Dye No. 401 | 0.01 |
| Yellow Dye No. 4 | 0.01 |
| Benzyl alcohol | 3.0 |
| Dipropylene glycol | 15.0 |
| Citric acid | 1.5 |
| Methylphenyl polysiloxane | 4.0 |
| Polyoxyethylene hydrogenated castor oil 40 E.O. | 1.0 |
| Hydroxyethyl cellulose | 2.5 |
| Purified water | Balance |

Preparation Method

A mixture of dipropylene glycol, benzyl alcohol, methylphenyl polysiloxane and polyoxyethylene hydrogenated castor oil 40 E.O. was dissolved in purified water, followed by the gradual addition of hydroxyethyl cellulose to prepare a viscous liquid. Black Dye No. 401, Purple Dye No. 401 and Yellow Dye No. 4 were then added to this viscous liquid after which the pH was adjusted to 3.5–3.8 with citric acid to obtain a uniform liquid.

Example 9

Color Rinse Type Hair Dye

| Formulation | |
|---|---|
| Black Dye No. 401 | 0.03(%) |
| Purple Dye No. 401 | 0.01 |
| Yellow Dye No. 4 | 0.01 |
| Benzyl alcohol | 3.0 |
| Dipropylene glycol | 15.0 |
| Citric acid | 1.5 |
| Decamethylcyclopentasiloxane | 21.0 |
| Dimethylpolysiloxane ($R_1$ and $R_2$ are methyl groups and n = 20,000 in the general formula of a polymer silicone indicated in the above-mentioned formula (9)) | 3.0 |
| Polyoxyethylene hydrogenated castor oil 40 E.O. | 3.0 |
| Hydroxyethyl cellulose | 2.0 |
| Purified water | Balance |

Preparation Method

A mixture of a majority of the dipropylene glycol and benzyl alcohol were dissolved in purified water, followed by the addition of a solution of decamethylcyclopentasiloxane, dimethylpolysiloxane, dipropylene glycol and polyoxyethylene hydrogenated castor oil 40 E.O.. Next, hydroxyethyl cellulose was gradually added to prepare a viscous liquid. Black Dye No. 401, Purple Dye No. 401 and Yellow Dye No. 4 were then added to this viscous liquid after which the pH was adjusted to 3.5–3.8 with citric acid to obtain a uniform viscous liquid.

Example 10

Color Rinse Type Hair Dye

| Formulation | |
|---|---|
| Black Dye No. 401 | 0.03(%) |
| Purple Dye No. 401 | 0.01 |
| Yellow Dye No. 4 | 0.01 |
| Benzyl alcohol | 1.5 |
| Citric acid | 1.5 |

| Formulation | |
|---|---|
| Hydroxyethyl cellulose | 2.5 |
| Purified water | Balance |

Comparative Example 2

Color Rinse Type Hair Dye

| Formulation | |
|---|---|
| Black Dye No. 401 | 0.03(%) |
| Purple Dye No. 401 | 0.01 |
| Yellow Dye No. 4 | 0.01 |
| Citric acid | 1.5 |
| Hydroxyethyl cellulose | 2.5 |
| Purified water | Balance |

When the dyeing properties of the hair dyes of Example 10 and Comparative Example 2 were compared, in contrast to the dyeing properties of Example 10, which were favorable, the dyeing properties of Comparative Example 2 were extremely poor, thereby preventing same from being used as a color rinse type of hair dye.

Example 11

Color Rinse Type Hair Dye

| Formulation | |
|---|---|
| Black Dye No. 401 | 0.03(%) |
| Purple Dye No. 401 | 0.01 |
| Yellow Dye No. 4 | 0.01 |
| Benzyl alcohol | 3.0 |
| Citric acid | 1.5 |
| Levulinic acid | 20.0 |
| Polyoxyethylene hydrogenated caster oil 40 E.O. | 1.0 |
| Hydroxyethyl cellulose | 2.5 |
| Purified water | Balance |

Preparation Method

A mixture of benzyl alcohol, levulinic acid and polyoxyethylene hydrogenated castor oil 40 E.O. was dissolved in purified water followed by the gradual addition of hydroxyethyl cellulose to prepare a viscous liquid. Black Dye No. 401, Purple Dye No. 401 and Yellow Dye No. 4 were then added to this viscous liquid after which the pH was adjusted to 3.5–3.8 with citric acid to obtain a uniform liquid.

Example 12

Color Rinse Type Hair Dye

| Formulation | |
|---|---|
| Black Dye No. 401 | 0.03(%) |
| Purple Dye No. 401 | 0.01 |
| Yellow Dye No. 4 | 0.01 |
| Benzyl alcohol | 3.0 |
| Citric acid | 1.5 |
| N-methylpyrolidone | 10.0 |
| Polyoxyethylene hydrogenated caster oil 40 E.O. | 3.0 |
| Hydroxyethyl cellulose | 2.0 |
| Purified water | Balance |

Preparation Method

A mixture of benzyl alcohol, N-methylpyrolidone and polyoxyethylene hydrogenated castor oil 40 E.O. was dissolved in purified water, followed by the gradual addition of hydroxyethyl cellulose to prepare a viscous liquid. Black Dye No. 401, Purple Dye No. 401 and Yellow Dye No. 4 were then added to this viscous liquid after which the pH was adjusted to 3.5–3.8 with citric acid to obtain a uniform liquid.

Example 13

Color Rinse Type Hair Dye

| Formulation | |
|---|---|
| Black Dye No. 401 | 0.03(%) |
| Purple Dye No. 401 | 0.01 |
| Yellow Dye No. 4 | 0.01 |
| Benzyl alcohol | 3.0 |
| Citric acid | 1.5 |
| Tetrahydrofurfuryl alcohol | 15.0 |
| Polyoxyethylene hydrogenated castor oil 40 E.O. | 1.0 |
| Hydroxyethyl cellulose | 2.5 |
| Purified water | Balance |

Preparation Method

A mixture of benzyl alcohol, tetrahydrofurfuryl alcohol and polyoxyethylene hydrogenated castor oil 40 E.O. was dissolved in purified water, followed by the gradual addition of hydroxyethyl cellulose to prepare a viscous liquid. Black Dye No. 401, Purple Dye No. 401 and Yellow Dye No. 4 were then added to this viscous liquid after which the pH was adjusted to 3.5–3.8 with citric acid to obtain a uniform liquid.

Examples 14–17

Color rinse type hair dyes were prepared using the formulated amounts indicated in Table 4 below. All of the resulting hair dyes demonstrated favorable dyeing properties.

TABLE 4

| Example No. | 14 | 15 | 16 | 17 |
|---|---|---|---|---|
| Black Dye No. 401 | 0.03 | 0.04 | 0.001 | 0.06 |
| Purple Dye No. 401 | 0.01 | 0.01 | 0.002 | 0.02 |
| Yellow Dye No. 406 | 0.01 | 0.005 | 0.005 | 0.02 |
| Benzyl alcohol | 2.0 | 1.0 | 10.0 | 1.5 |
| Citric acid | 1.0 | 1.0 | 2.5 | 1.0 |
| Tetrahydrofurfuryl alcohol | 2.0 | — | 7.0 | — |
| POE cured castor oil 40 E.O. | 1.0 | 1.0 | 0.5 | 1.5 |
| Hydroxyethyl cellulose | 2.5 | 2.5 | 2.5 | 2.5 |
| N-methylpyrolidone | — | 2.5 | 6.0 | — |
| 1,3-butylene glycol | — | — | — | 5.0 |
| Levulinic acid | 5.0 | 2.5 | 5.0 | — |
| Purified water | Balance | Balance | Balance | Balance |

INDUSTRIAL APPLICABILITY

As mentioned above, according to the present invention, an acid dye composition for hair is provided demonstrating favorable dyeing properties and anti-washability as well as a supple texture following use. In addition, by taking advantage of the single preparation, characteristic of the present hair dye composition it can be applied as a hair dye composition over a broad range, including a combined rinse and shampooing.

Moreover, according to the present invention, although the formulating amount of dye is reduced when used as a combination rinse and hair dye composition, a hair dye composition can still be obtained that demonstrates dyeing properties that are satisfactory in terms of practical use.

I claim:

1. An acid dye composition for hair comprising:
   (A) 1% to 10% by weight of benzyl alcohol,
   (B) 0.001% to 0.1% by weight of an acid dye, and
   (C) 0.01% to 5.0% by weight of at least one polysiloxane, all based upon the total amount of the composition, the ratio (A)/(B) being 15 to 1250 and the pH of the composition being 1.5 to 4.5.

2. An acid dye composition for hair as according to claim 1 which further comprises 5% by weight or more of at least one compound selected from the group consisting of levulinic acid, N-methylpyrolidone and tetrahydrofurfuryl alcohol.

3. An acid dye composition for hair according to claim 1 which further comprises 5% by weight or more of at least one polyol.

4. An acid dye composition for hair according to claim 3, wherein said polysiloxane is at least one compound selected from the group consisting of (A) Dimethylpolysiloxane

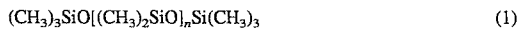
$(CH_3)_3SiO[(CH_3)_2SiO]_nSi(CH_3)_3$ (1)

wherein, in the formula (1), n is an integer from 3–650, (B) Methylphenylpolysiloxane

$(CH_3)_3SiO(SiO)_nSi(CH_3)_3$ with $C_6H_5$ and $CH_3$ substituents (2)

$(CH_3)_3SiO[(CH_3)_2SiO]_n[C_6H_5)_2SiO]_mSi(CH_3)_3$ (3)

wherein, in the formula (2), n is an integer from 1–500, and in the formula (3), the sum of m and n is an integer of 1–500, (C) Polyether denatured polysiloxane

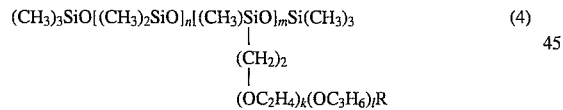
$(CH_3)_3SiO[(CH_3)_2SiO]_n[(CH_3)SiO]_mSi(CH_3)_3$ with $(CH_2)_2(OC_2H_4)_k(OC_3H_6)_lR$ substituent (4)

wherein, in the formula (4), R represents an alkyl group having 1–12 carbon atoms, an alkoxy group having 1–6 carbon atoms or a hydroxyl group, n represents an integer from 1–100, m represents an integer from 1–20, k represents an integer from 0–50, and l represents an integer from 0–50, (D) Amino modified polysiloxane $R(CH_3)_2SiO[(CH_3)_2SiO]_n$-
$[(CH_3)(CH_2CH_2CH_2NHCH_2CH_2NH_2)SiO]_mSi(CH_3)R$ (5)

$R(CH_3)_2SiO[(CH_3)_2SiO]_n$-$[(CH_3)(CH_2CH_2CH_2NH_2)SiO]_mSi(CH_3)R$ (6)

wherein, in the formulae (5) and (6), R represents a methyl group or methoxy group, n represents an integer of 1–500, and m represents an integer of 1–50, (E) Epoxy modified polysiloxane

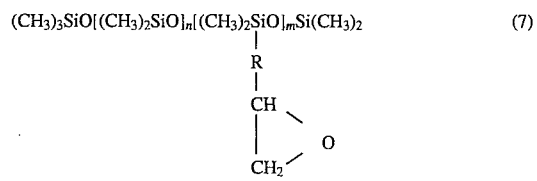
$(CH_3)_3SiO[(CH_3)_2SiO]_n[(CH_3)_2SiO]_mSi(CH_3)_2$ with R–CH–CH$_2$–O substituent (7)

wherein in the formula (7), R represents an alkylene group having 1–3 carbon atoms, n represents an integer of 1–500 and m represents an integer of 1–50, (F) Fluorine modified polysiloxane

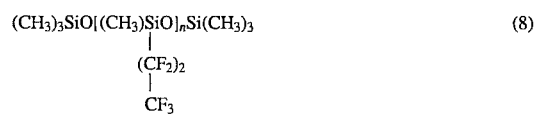
$(CH_3)_3SiO[(CH_3)SiO]_nSi(CH_3)_3$ with $(CF_2)_2CF_3$ substituent (8)

wherein, in the formula (8), n represents an integer from 1–400, (G) Alcohol modified polysiloxane $HO(CH_2)R[(CH_3)_2SiO]_n(CH_3)_2SiRCH_2OH$ (9)

$(CH_3)_3SiO[(CH_3)_2SiO]_n[(CH_3)SiO]_mSi(CH_3)_3$ with R—CH(OH)CH$_3$ substituent (10)

wherein, in the formulae (9) and (10), R is absent or represents an alkylene group having 1–4 carbon atoms, and n and m represent integers of 1–500 and 1–200, respectively, (H) Alkyl modified polysiloxane

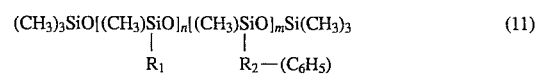
$(CH_3)_3SiO[(CH_3)_2SiO]_n[(CH_3)SiO]_mSi(CH_3)_3$ with $R_1$ and $R_2$—$(C_6H_5)$ substituents (11)

$(CH_3)_3SiO[(CH_3)_2SiO]_n[(CH_3)SiO]_mSi(CH_3)_3$ with $R_3$ substituent (12)

wherein, in the formulae (11) and (12), $R_1$ represents an alkyl group having 2–18 carbon atoms, $R_2$ is absent or represents an alkylene group having 1–4 carbons, $R_3$ represents an alkyl group having 10–16 carbons, and n and m are integers of 1–500 and 1–200, respectively, and (I) High polymer silicone

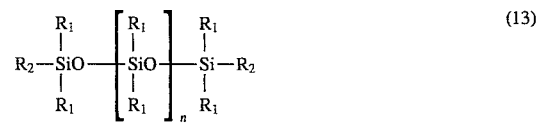
(13)

wherein, in the formula (13), $R_1$ each individually represents a methyl group or a phenyl group, $R_2$ represents a methyl group or hydroxyl group, and n represents an integer from 3,000–20,000.

5. An acid dye composition for hair according to claim 3, wherein the polyol comprises at least one member selected from the group consisting of methyl ethyl cellosolve, methyl ethyl carbitol, 1,3-butylene glycol, dipropylene glycol and propylene glycol.

* * * * *

UNITED STATES PATENT AND TRADEMARK OFFICE
CERTIFICATE OF CORRECTION

PATENT NO : 5,601,620
DATED : February 11, 1997
INVENTOR(S): Ishikawa, Hiroshi

It is certified that error appears in the above-identified patent and that said Letters Patent is hereby corrected as shown below:

Title Page [30] Foreign Application Priority Data; Delete " Feb. 14, 1992 " and substitute -- Feb. 15, 1991 --

Signed and Sealed this

Fifth Day of October, 1999

Attest:

Q. TODD DICKINSON

Attesting Officer

Acting Commissioner of Patents and Trademarks